(12) United States Patent
Cohen et al.

(10) Patent No.: US 7,608,447 B2
(45) Date of Patent: Oct. 27, 2009

(54) PULSE-MEDIUM PERFUSION BIOREACTOR WITH IMPROVED MASS TRANSPORT FOR MULTIPLE-3-D CELL CONSTRUCTS

(75) Inventors: Smadar Cohen, Beer Sheva (IL); Tal Dvir, Rishon LeZion (IL); Michal Shachar, Beer Sheva (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 374 days.

(21) Appl. No.: 10/581,848

(22) PCT Filed: Dec. 9, 2004

(86) PCT No.: PCT/IL2004/001118

§ 371 (c)(1),
(2), (4) Date: Jan. 8, 2007

(87) PCT Pub. No.: WO2005/056747

PCT Pub. Date: Jun. 23, 2005

(65) Prior Publication Data

US 2007/0111310 A1     May 17, 2007

(51) Int. Cl.
*C12M 1/00*     (2006.01)
(52) U.S. Cl. .................................... 435/299.1
(58) Field of Classification Search ........................ None
See application file for complete search history.

(56) References Cited

U.S. PATENT DOCUMENTS 5,057,428 A    10/1991    Mizutani et al.
5,068,195 A    11/1991    Howell et al.

FOREIGN PATENT DOCUMENTS

EP    0 365 313    4/1990
EP    0 725 134    8/1996

OTHER PUBLICATIONS

ISR for WO 2005/056747 A3—3 pages, (2005).
Shachar M., et al., (2003) Ex-vivo engineering of cardiac muscle: Cultivation in rotating vessels. Proceedings of EMCC-Bioengineering.

*Primary Examiner*—James S Ketter
(74) *Attorney, Agent, or Firm*—Roach Brown McCarthy & Gruber, P.C.; Kevin D. McCarthy

(57) ABSTRACT

Disclosed is a novel net member for supporting one or more cell constructs in the culture chamber of a bioreactor, which comprises an array of impermeable pyramidal elements protruding from the face thereof, wherein each of the corners of the base of each of said impermeable pyramidal elements comprises a circular opening. This net member provides for uniform and unobstructed flow of culture medium through 3D cell constructs in culture.

Also disclosed are a bioreactor and bioreactor system incorporating said net member.

The bioreactor and bioreactor system may be used in the bioproduction of therapeutic proteins and stem cell expansion.

39 Claims, 15 Drawing Sheets

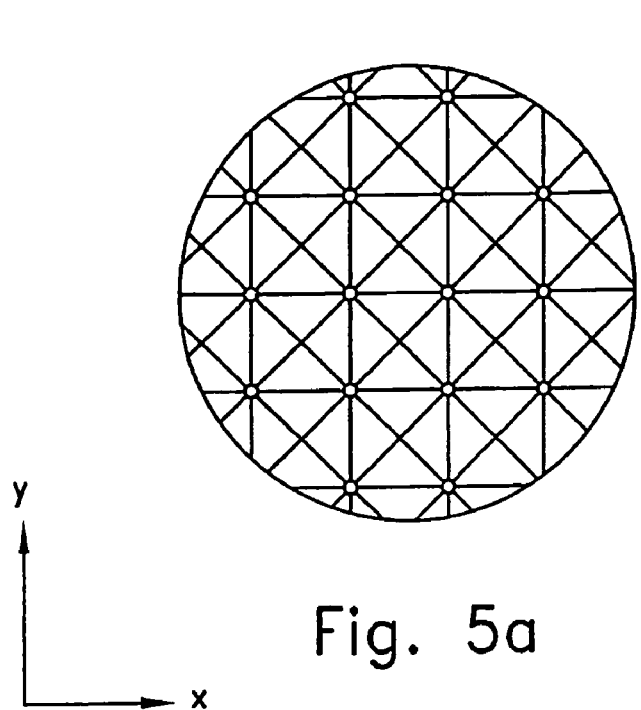
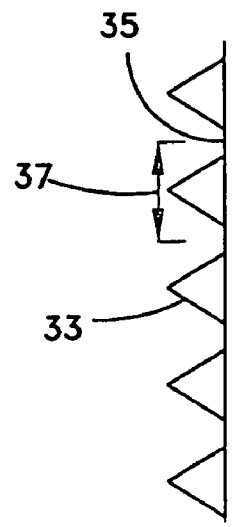
Fig. 5a
Fig. 5b
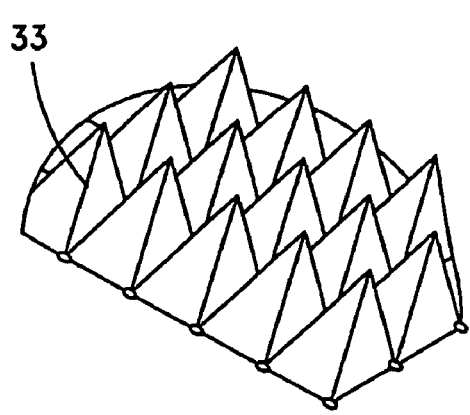
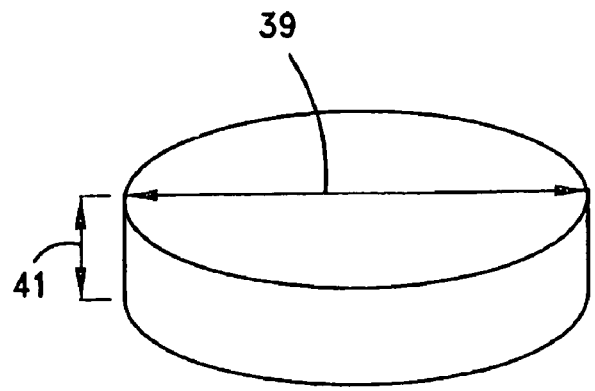
Fig. 5c
Fig. 5d

PULSE-MEDIUM PERFUSION BIOREACTOR WITH IMPROVED MASS TRANSPORT FOR MULTIPLE-3-D CELL CONSTRUCTS

FIELD OF INVENTION

The present invention is related to three dimensional (3-D) cell cultures. More particularly, the present invention is related to a bioreactor designed for supporting the cultivation of cells in three dimensional constructs for use as medical implants and in biotechnological processes such as bioproduction of therapeutic proteins and cell expansion.

BACKGROUND OF INVENTION

All publications mentioned throughout this application are fully incorporated herein by reference, including all references cited therein.

Tissues in the body contain spaced capillaries that provide conduits for the convective transport of nutrients and waste products to and from the tissues. However, cell constructs that are developed ex-vivo usually lack the vascular network that exists in normal vascularized tissues. Hence, the gas and nutrient supply to and from ex-vivo cell constructs depends solely on mass transport (e.g. diffusion) of the growth medium.

It is well known that bioreactors that are employed to cultivate cell constructs are designed to improve the mass transport of nutrients and other products within the growing tissues. Various kinds of bioreactors make use of different patterns of fluid dynamics and vessel geometry. Ideally, bioreactors must allow for control over the physicochemical environment (e.g. $pO_2$, pH, $pCO_2$, shear stress, etc.), allow for aseptic feeding and sampling in order to follow tissue development and maximize the use of automated processing steps in order to increase reproducibility.

Standard bioreactor technologies that are known in the art are well suited for addressing the many issues involved in 2-D cell expansion, but have limitations when used for other tissue engineering applications. For example, the cultivation of 3-D tissue constructs places large demands on the mass transport requirement (e.g. nutrient distribution). Furthermore, it is sometimes necessary to simultaneously culture multiple cell types for a certain application, which would require more complex bioreactor designs.

The present inventors have previously reported the cultivation of cardiomyocytes constructs in rotating cell culture systems (RCCS), which were developed by NASA (see Shachar M., et al., (2003) Ex-vivo engineering of cardiac muscle: Cultivation in rotating vessels. Proceedings of EMCC-Bioengineering). The operating principles of the RCCS are solid body rotation about a horizontal axis, which is characterized by extremely low fluid shear stress, and oxygenation by active or passive diffusion of dissolvable gasses from the reactor chamber, thereby yielding a vessel devoid of gas bubbles and gas/fluid interfaces. The present inventors showed that $pO_2$, pH and $pCO_2$ were maintained in the RCCS to a better extent, and aerobic respiration was allowed for a larger number of cells, as compared to performance in a static vessel. Cultivation of cardiac cell constructs in RCCS produced engineered cardiac tissues with improved cellularity, cell metabolism and expression of muscle specific markers.

Although the RCCS provided a nearly homogeneous ex-vivo environment for the 3-D cell constructs, the extent of medium perfusion into the core of the cultivated tissue was still limited due to the absence of a capillary network in the developing tissue. As a result, the cells at the center of the 3-D cultivated tissues did not benefit from the external dynamic fluid.

It is therefore an aim of the present invention to provide a bioreactor system that overcomes the problems involved in previous bioreactor systems, specifically poor mass transfer.

It is another aim of the present invention to provide a bioreactor system that enhances mass transport of a desired medium into a developing tissue.

It is another aim of the present invention to provide a bioreactor system which pumps a growth medium directly through 3-D cell-seeded scaffolds.

It is another aim of the present invention to provide a bioreactor system which pumps a growth medium through a 3-D cell-seeded scaffold in a similar manner to the pumping activity of a heart.

Other aims and advantages of the present invention will become apparent as the description proceeds.

SUMMARY OF INVENTION

In a first aspect, the present invention relates to a net for supporting one or more cell constructs in the culture chamber of a bioreactor, comprising an array of impermeable pyramidal elements protruding from the face of said net, wherein each of the corners of the base of each of said impermeable pyramidal elements comprises a circular opening. The diameter of said circular opening may preferably between be 0.1 mm to 3 mm, and more preferably, 1.25 mm. The distance between any two adjacent circular openings situated orthogonally to one another along the x- or y-axis is preferably between 1 mm to 10 mm, and more preferably, 3 mm. The angle of the outer edges of the pyramidal elements of the net of the invention are preferably between 1° to 179°, and more preferably, 60°.

Specifically, the net may be preferably constructed from Plexiglas™, polycarbonate or any other solid transparent material.

In a second aspect, the invention relates to a bioreactor comprising an inlet half having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and further comprising at least one net in accordance with the invention, wherein said net is positioned transversely within said culture chamber at a predetermined distance from said inlet aperture.

In specific embodiments, the culture chamber of the bioreactor of the invention is cylindrical in shape and the net is substantially circular. The diameter of the net may be substantially equal to the diameter of said culture chamber, or smaller.

In yet another preferred embodiment, the bioreactor of the invention comprises two substantially identical nets of the invention, preferably positioned transversely within said culture chamber at a predetermined distance from each other. In such embodiment, at least one of said nets may be permanently affixed to the circumference of said culture chamber, and the other net is removably affixed within the chamber. The bioreactor thus may comprise means for removably affixing at least one of said nets within said culture chamber, for example a projection which protrudes inward from the circumference of said culture chamber wall.

In particular embodiments, the said inlet aperture of the bioreactor of the invention may be threaded for suitably attaching means for transferring a fluid medium to said culture chamber, and also the said outlet aperture may be suitably threaded for attaching means for transferring fluid medium from said culture chamber. Such means may comprise suitable transfer tubing.

The said inlet half and said outlet half of the bioreactor of the invention may be joined to each other via suitable means such as screws or bolts, or an O-ring.

The bioreactor may further comprise at least one fluid distributor mesh, positioned in said inlet half between said inlet aperture and said net and/or in said outlet half between said outlet aperture and said net. The fluid distributor mesh preferably has pores of a diameter which is preferably up to 10 mm, and more preferably 2 mm.

The bioreactor of the invention may be used for bioproduction of therapeutic protein, and for other processes, for example stem cell expansion.

In a further aspect, the invention relates to a bioreactor system comprising:

a. a bioreactor comprising an inlet half having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and comprising two substantially identical nets for supporting at least one cell construct in said chamber, wherein the distance between said nets is substantially equal to the thickness of said at least one cell construct, wherein each of said nets comprises an array of pyramidal elements protruding from the face of said net, wherein the vertex of each of said pyramidal elements comprises a circular opening;

b. a culture medium reservoir for storing a supply of a fluid culture medium, comprising a medium inlet and outlet, and further comprising a gas inlet and outlet;

c. a gas supply for supplying gas to said medium contained in said reservoir;

d. a heat exchanger for maintaining the temperature of said medium at a constant value, and e. a pump for pumping said medium from said reservoir into said bioreactor and back to said reservoir.

The reservoir of the bioreactor system of the invention preferably comprises a medium sample collection outlet. The pump is preferably a peristaltic pump.

In yet a further aspect, the invention relates to a method for the cultivation of 3-D cell constructs, comprising the following steps:

a. providing a bioreactor system comprising:
  i. a bioreactor, said bioreactor comprising an inlet half having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and comprising two substantially identical nets for supporting at least one cell construct in said chamber, wherein the distance between said nets is substantially equal to the thickness of said at least one cell construct, wherein each of said nets comprises an array of pyramidal elements protruding from the face of said net, wherein the vertex of each of said pyramidal elements comprises a circular opening;
  ii. a culture medium reservoir for storing a supply of a fluid culture medium, comprising a medium inlet and outlet;
  iii. a gas supply for supplying gas to said medium contained in said reservoir;
  iv. a heat exchanger for maintaining the temperature of said medium at a constant value; and
  v. a pump for pumping said medium from said reservoir into said bioreactor and back to said reservoir;

b. placing at least one cell construct within said culture chamber, between said nets;

c. pumping said medium from said reservoir into said culture chamber, thereby causing medium perfusion into said cell construct for a suitable period of time; and d. harvesting the resulting construct.

The method of the invention may optionally further comprise the steps of:

e. removing a sample of said medium from said reservoir after step c and before step d, in order to determine whether said medium should be replaced with new medium; and f. adding fresh medium to said reservoir when necessary, after optional step e and before step d.

The said cell construct preferably consists of a polymeric scaffold seeded with cells, more preferably the said polymer is a polysaccharide, particularly alginate.

The said cells are human cells, preferably cardiomyocytes.

The 3-D cell constructs produced by method of the invention are particularly useful for the bioproduction of therapeutic proteins or for stem cell expansion The invention will be described in more detail on hand of the accompanying Figures.

BRIEF DESCRIPTION OF FIGURES

FIG. 5 illustrates a preferred embodiment of a net of the present invention in front (5a), side (5b) and partially sectioned perspective (5c) views; FIG. 5d schematically illustrates a cell construct for use with the present invention in perspective view.

DETAILED DESCRIPTION OF THE INVENTION

The present invention is directed to improving the cultivation of 3-D cell constructs. Generally, in accordance with the present invention, a pulse-medium perfusion bioreactor (PMPB) is provided, which is designed to improve the mass transport of a growth medium into cultivating 3-D cell constructs. The improvement is achieved via perfusion, by replicating the heart physiology, wherein pulses of oxygenated blood are sent to the different tissues of the body. In the present invention, a peristaltic pump provides pulsation of the medium, and the rates of pulsation and perfusion are preferably computer-controlled. The culture medium is forced directly into the 3-D cell constructs via a specially designed flow directing net, thereby enhancing nutrient distribution within the cell constructs. This net constitutes a specific aspect of the present invention.

The term "medium" or "growth medium" or "culture medium" as used herein, refers to a fluid containing the nutrients and dissolved gases that are necessary for the growth of viable cells in cell or tissue culture, seeded or contained in a cell construct.

The term "construct" as used herein means a porous support structure, preferably made of a biocompatible polymer, which can mechanically support cell/s seeded therein, and can be used as a "growth field" or as a scaffold for the seeded cells. The terms "construct" and "scaffold" are used herein interchangeably.

The term "cell construct" as used herein, refers to a construct, as herein defined, which has been seeded with cells. The cell construct can be placed within a cell growth medium or environment, such as the culture chamber of a bioreactor. This term may be used interchangeably with "construct".

The term "culture chamber" (or "chamber") as used herein, refers to the hollow interior or lumen of a bioreactor, in which cells, tissue or cell constructs are placed, and through which medium passes.

In a first embodiment, the invention thus relates to a bioreactor system.

Figure 1:
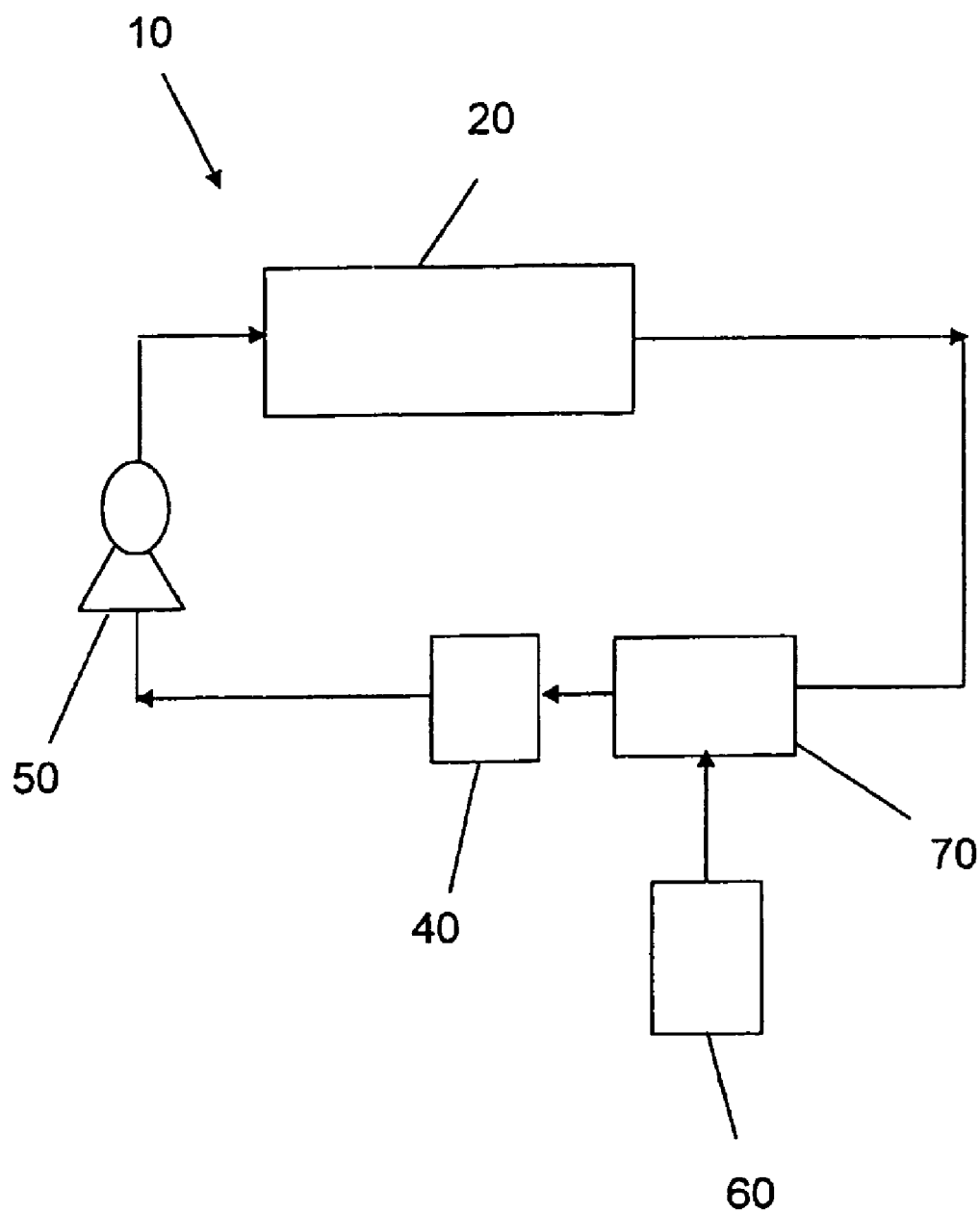
FIG. 1 illustrates in a block diagram, the bioreactor system of the present invention in a preferred embodiment.

Referring to FIG. 1, a preferred embodiment of the present invention is shown in a block diagram wherein a bioreactor system, generally designated with the numeral (10), comprises a bioreactor body (20), an oxygenated medium reservoir (70), a computerized peristaltic pump (50), a heat exchanger (40) and a gas supply source (60). The arrows show the direction of the circulation of the medium within the system. The medium is pumped through suitable tubing from the reservoir (70) into the bioreactor (20) by the peristaltic pump (50), and then proceeds back to the reservoir (70), where it is oxygenated and buffered with $CO_2$ by the gas supply (60) and pumped back to the bioreactor (20). At any suitable time, the medium may be removed from the reservoir (70) and replaced with fresh medium, as described herein below. The heat exchanger (40) maintains the medium in constant temperature throughout the process.

In a second embodiment, the invention relates to a bioreactor, which can be particularly used with the bioreactor system of the invention.

Figure 2:
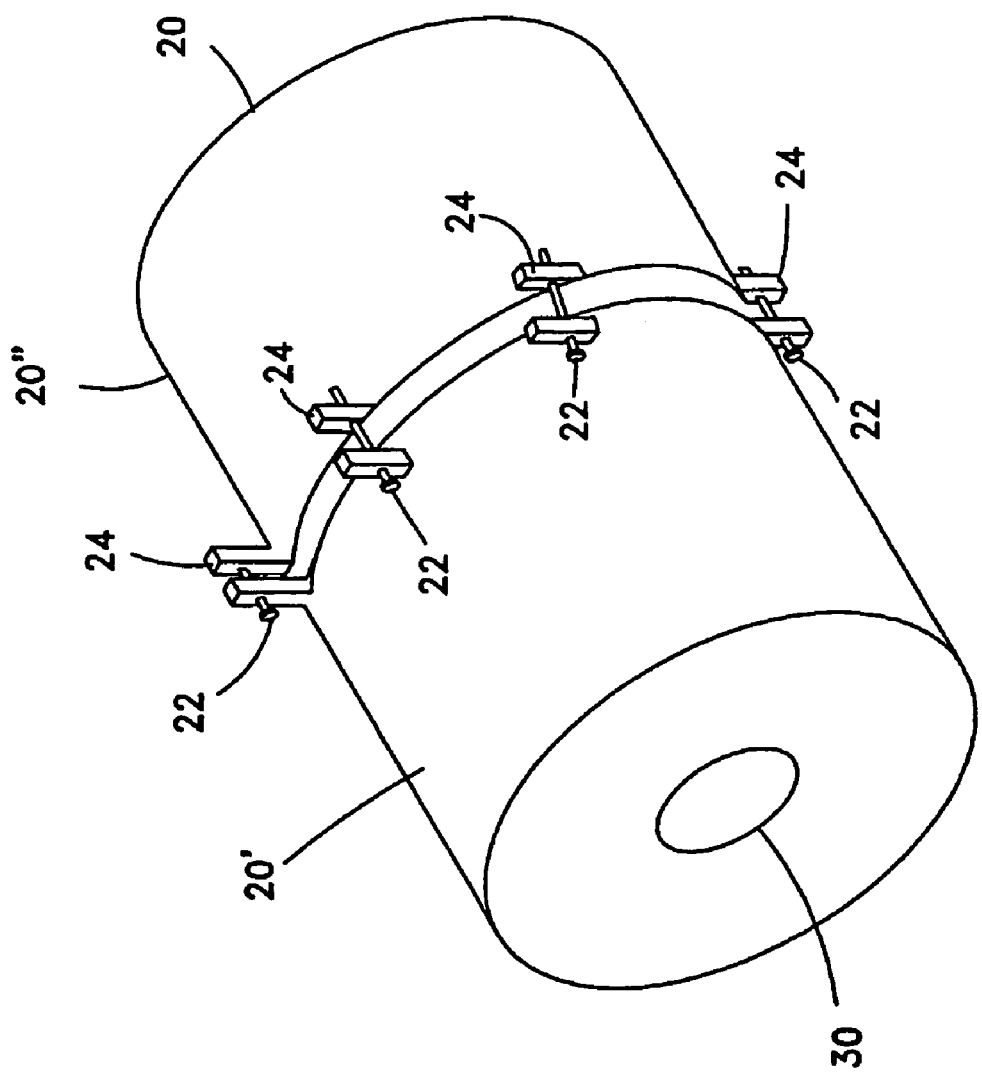
FIG. 2 illustrates a preferred embodiment of the bioreactor of the present invention in isometric view.

In a preferred embodiment, the bioreactor (20) of the present invention, as can be seen in FIG. 2, has a substantially cylindrical configuration. The bioreactor (20) comprises two symmetric hollow halves, inlet half (20') and outlet half (20"), wherein the halves (20'), (20") are joined to each other for example by bolts (22) that are inserted at holes in each one of six flanges (24). The bioreactor may be constructed from any material that is inert or biocompatible with the growth medium, and possesses the physical strength to withstand pressures of fluid flow. Preferred materials are Plexiglass™, polycarbonate or any solid transparent material. For reusable bioreactors, the material should resist sterilization by autoclaving. For disposable bioreactors (i.e. a single use) any inert material may be used.

A cross-section taken longitudinally along the bioreactor (20) (FIG. 3) shows the internal geometry of a preferred embodiment of the culture chamber (26), wherein cells, tissue or 3-D cell constructs are cultivated. The chamber (26) has a cylindrical configuration which is formed by joining the two bioreactor halves (20'), (20") together, as described above, and sealing the halves by an O-ring (not shown) that is located in groove (28). The medium is introduced to the chamber (26) through inlet aperture (30) and exits through outlet aperture (32). The internal walls of the inlet (30) and outlet (32) apertures are preferably threaded for suitably attaching tubing or other means for transferring the medium to and from the bioreactor (20), respectively. The diameter of the inlet aperture (30) is preferably between 0.1 mm to 15 mm. In this preferred configuration, the inner walls of the bioreactor taper towards the inlet (30) and outlet (32), preferably at and angle of between 1 to 89 degrees, and more preferably, 30 degrees in order to avoid turbulence and maintain the flow vector. Increasing the cross-sectional area of the chamber in the direction of the flow of the medium prevents the disruption of the incoming flow, and thus avoids turbulence, as described herein below. The chamber (26) diameter may preferably range between 5 mm to 250 mm, and more preferably between 50 mm to 80 mm.

The description of the construction of the bioreactor chamber (26) given herein is according to a preferred embodiment represented in the Figures, but dimensions may be scaled according to the desired need. It should be noted that other designs of the bioreactor are contemplated by the present invention and that skilled persons, utilizing the principles of the description given herein, can readily devise these designs.

Figure 3:
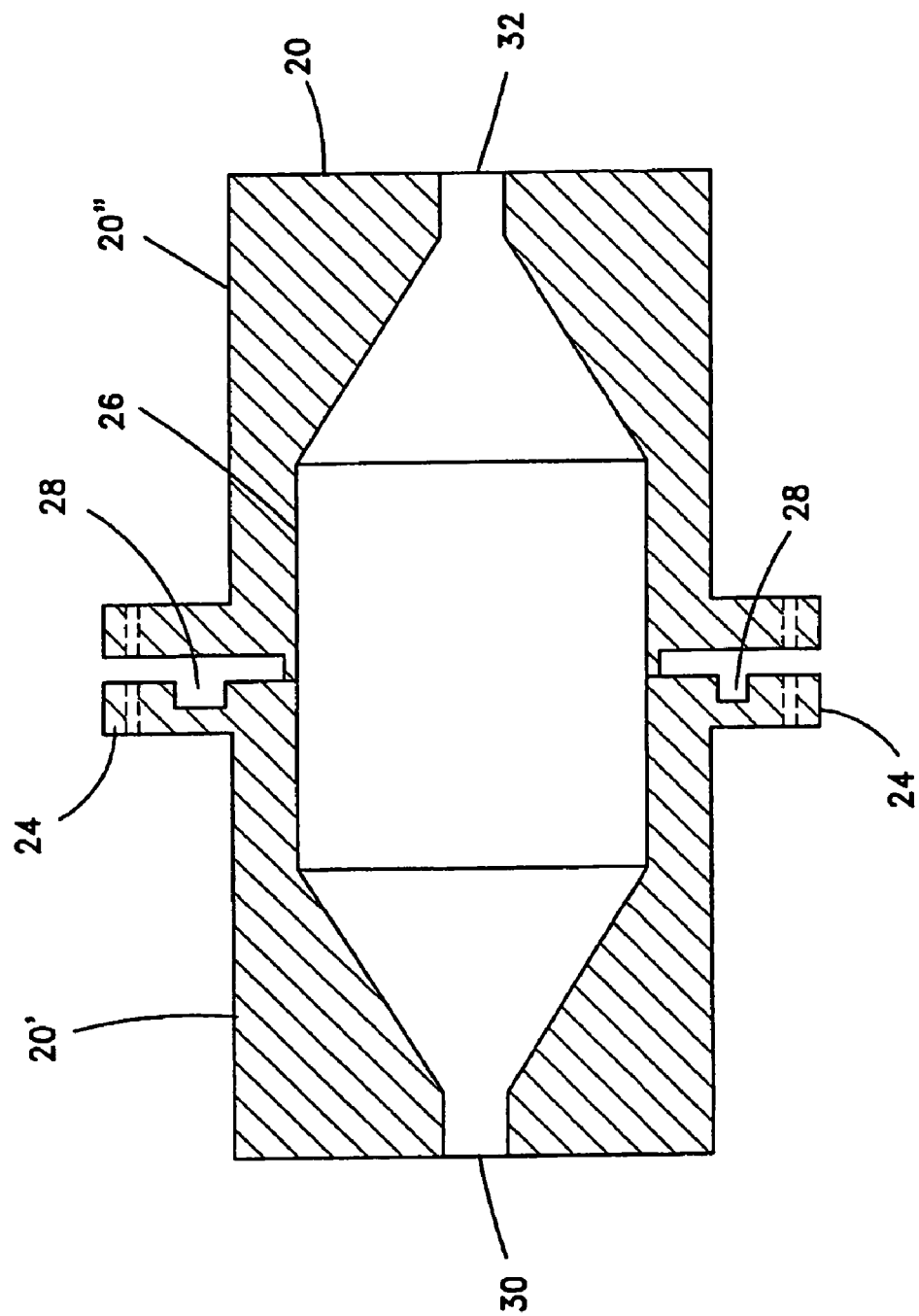
FIG. 3 illustrates a longitudinal cross-sectional view of the bioreactor of FIG. 2, showing the culture chamber.
Figure 4:
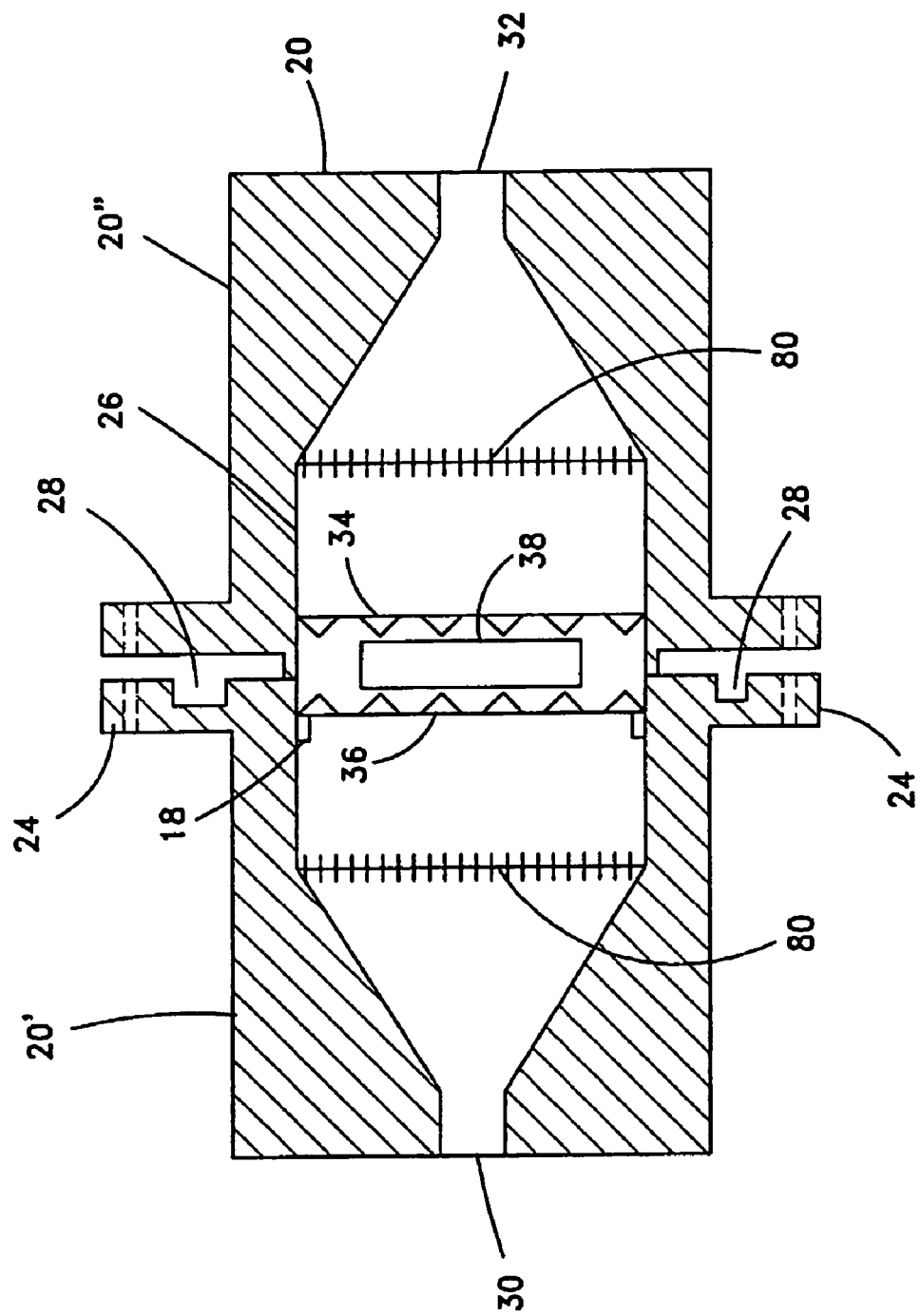
FIG. 4 illustrates the same view of FIG. 3, schematically showing 3-D cell constructs being held in place by nets positioned within the culture chamber.

FIG. 4 shows schematically, the cell chamber of the bioreactor of FIG. 3, provided with two net members (34), (36), wherein at least one cell construct (38) is fixed in place therein in order to support and prevent displacement of the construct (38) within the chamber (26). The nets may be constructed from any material that is inert or biocompatible with the growth medium, and possesses the physical strength to withstand pressures of fluid flow. Preferred materials are Plexiglas™, polycarbonate or any solid transparent material. For reusable nets, the material should resist sterilization by autoclaving. For disposable nets (i.e. a single use) any inert material may be used. Net member (34) is permanently secured to the chamber (26) walls by glue or other suitable means, and net member (36) may be removably affixed within the chamber (26), being held in place along one longitudinal direction of the chamber (26) by a projection (18) which protrudes inward from the circumference of the chamber (26) wall. Alternatively, net member (36) may be permanently secured to the chamber (26) walls, and net (34) may be removably affixed within the chamber (26).

A net member may be placed in both the inlet (20') and outlet (20") halves of the chamber respectively, in order to be suitably configured for reversible operation, wherein the parameters in the computerized pump may be set to reverse the medium flow direction. Reversible operation is desirable, for example, in order to enable a better cell distribution and to achieve similar normal stress throughout the cell construct(s). When unidirectional flow is desired, only one net is required to be placed within the chamber (26). The cell construct may then be supported at one side by the net of the present invention, and at the other side, by any suitable securing means. Where only one net of the present invention is situated within the chamber, the net is positioned between the inlet aperture (30) and the cell construct (38).

The nets (34), (36) shown in FIG. 4 are situated substantially at the central portion of the chamber along the longitudinal axis, such that one net is positioned in the inlet half (20') and the other net is positioned in the outlet half (20"). According to another embodiment, the two nets (34), (36) may both be situated in the inlet half (20'), or, alternatively, the two nets (34), (36) may both be situated in the outlet half (20"). According to either embodiment, the cell construct (38) is situated in between the two nets (34), (36).

Thus, in a further embodiment the invention relates to a flow directing net, for use in a bioreactor, particularly a bioreactor in accordance with the invention.

Figure 5E:
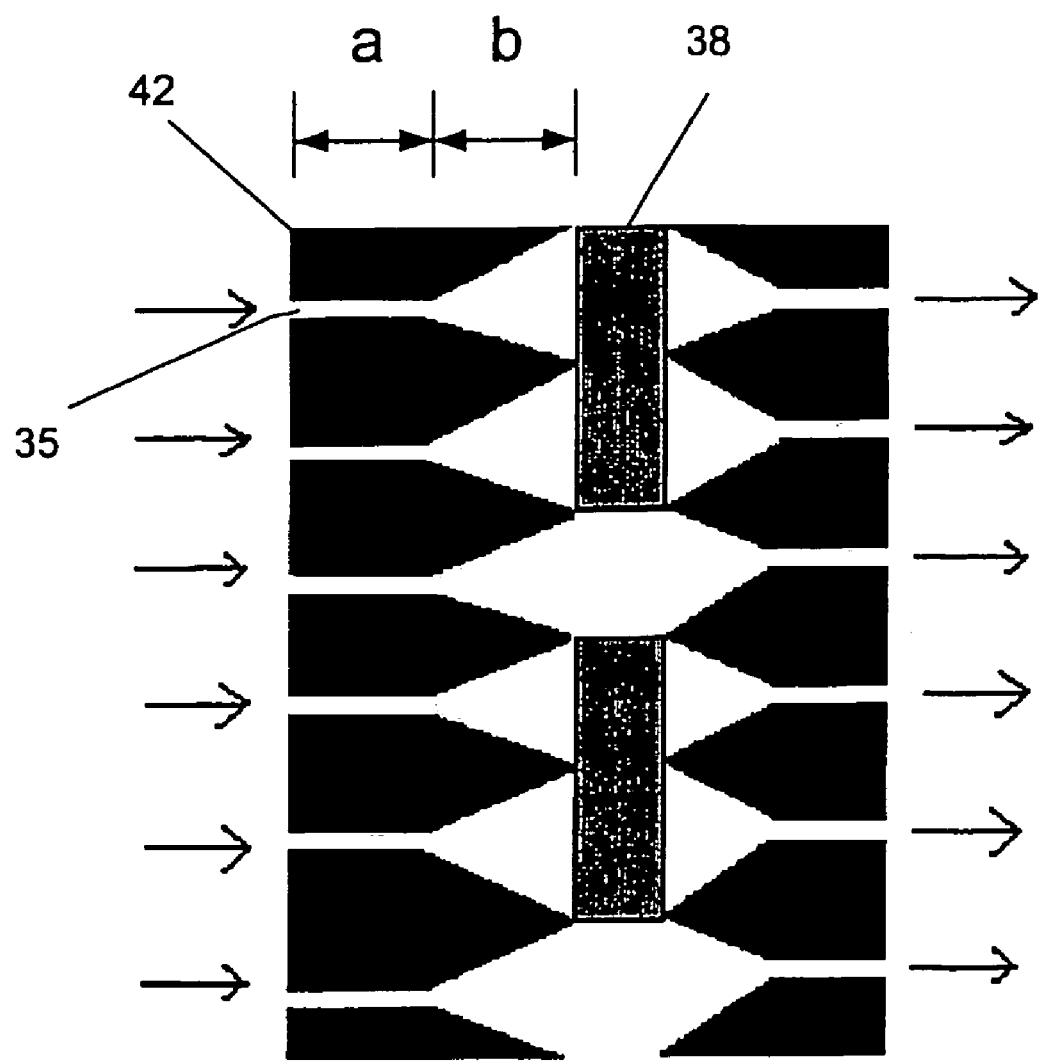
FIG. 5e schematically illustrates two cell constructs situated in between two nets, wherein the nets are shown with substantial thickness.

A preferred embodiment of a net is shown in more detail in FIGS. 5a-5c. FIG. 5a shows the net in front view, wherein the diameter of the net is substantially equal to the diameter of the chamber (26). FIG. 5b shows the net in side view, wherein substantially circular openings (35) are located at the corners of the base of the impermeable protruding pyramidal elements (33). The openings (35) preferably have a diameter of between 0.1 mm to 3 mm, and more preferably, a 1.25 mm diameter, determined according to the dimensions of the cell construct used, as described herein below. The distance between any two openings (35) located orthogonally to one another along the x- or y-axis (see FIG. 5a) is preferably between 1 mm to 10 mm, and more preferably 3 mm, determined according to the dimensions of the cell construct used, as described herein below, and in proportion to the diameter of the circular openings (35) and the scaffolds. FIG. 5c shows the net in a partially sectioned perspective view, wherein pyramidal elements (33) are shown protruding from the face of the net. The openings (35) may be essentially coplanar with the base such that the openings (35) are located substantially at the corners of the base, or, the base may extend (a) outward (FIG. 5e) to a maximum distance of preferably 20 mm, more preferably between 5 mm to 10 mm, most preferably 2 mm, depending on the thickness of the cell constructs (38) that are situated in between the nets, as described herein below, as well as the distance between the two nets. The height (b) of the pyramidal elements (33) (i.e. the distance between the base and the vertex) typically remains at a predetermined value. The angle of the outer edges of the pyramidal elements are preferably between 1° to 179°, and more preferably, 60°.

The geometry of the net ensures maximal exposure of the entire cell construct to the perfusing medium, and assists in the transport of medium into the cell construct. As can be seen in FIG. 5e, the medium passes through the openings (35) in the direction of the arrows, and is guided along the outer surface of the impermeable protruding pyramidal elements (33) until the medium reaches the cell constructs. Hence, the only portion of the surface of the cell construct that is not directly reached by the medium is the point of contact between the vertex of the pyramidal element (33) and the cell construct. This net design differs from that of conventional supporting nets that have typically been used in the prior art, which mask parts of the constructs from the medium flow.

Although the pyramidal elements that are shown in the figures comprise a base having a substantially square shape, the pyramidal elements may alternatively comprise a base having any polygonal shape, mutatis mutandis.

A typical cell construct (38) which may be utilized in the present invention is shown in FIG. 5d in perspective view. The thickness (41) of a typical construct (38) may range in size preferably from 1 mm to 1 cm, and the diameter (39) of a typical construct (38) may range in size preferably from 1 mm to as large as the diameter of the chamber (26). Thus, while only one cell construct (38) occupying only part of the diameter of the chamber (26) is shown in FIG. 4, this is for illustrative purposes only, and a construct (38) may occupy the entire diameter of the chamber (26), or alternatively, a plurality of smaller constructs (38) could occupy the same. Moreover, it should be noted that even with only one cell construct (38) being situated in between nets (34), (36) (FIG. 4), the desired perfusion of the medium within the construct (38) is obtained, irrespective of the relative position of construct (38) within the chamber (26) walls. While a substantially disc shaped construct is shown in FIG. 5d, other configurations such as square, rectangular or asymmetrical are of course possible.

As mentioned above, the purpose of the net is to direct the flow of the medium. In order to determine whether the flow in the chamber is laminar or turbulent, Reynolds number is calculated using the following equation:

$$Re = V * d / \nu$$

where V is the medium's average velocity, d is the diameter of the chamber and $\nu$ is the kinematic viscosity.

The average velocity can be calculated from the equation:

$$Q = V * A$$

where Q is the flow rate, and A is the cross section area of the bioreactor body at the compartment area.

The flow rate is determined based on mass transport and cell consumption, while taking into account the need to minimize stress on the cells. In a typical example, Q is set to be 150 ml/min, and $A = \pi d^2/4$ where d is 0.05 m, the cross section area is:

$$A = 1.96 * 10^{-3} \, m^2$$

Thus, the average velocity in the chamber (26) is:

$$V = Q/A = 1.28 * 10^{-3} \, m/s$$

The kinematic viscosity of the medium at 37° C. is assumed to be very close to the kinematic viscosity of water at 37° C., so $$\nu = 0.7 * 10^{-6} \, m^2/s$$

Thus, Reynolds number is:

$$Re = 91.4$$

Since laminar flow is defined as flow having a Reynolds number less than 2000, the medium flow inside the bioreactor (20) is seen to be laminar.

Figure 6A:
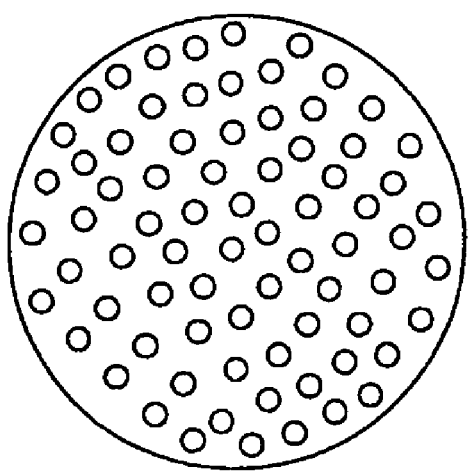
FIG. 6 illustrates a preferred embodiment of the mesh of the present invention in front view (6a), the velocity profile of a laminar developed flow in a pipe (6b) and in a pipe before and after a mesh is added (6c).
Figure 6B:
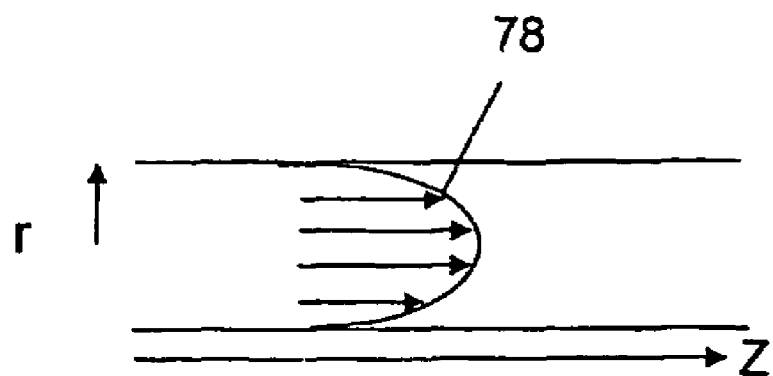

The Navier-Stokes profile of a developed laminar flow velocity (78) in a pipe (FIG. 6b) is calculated according to the following equation:

$$V_z = \frac{(\Delta P)}{4L\mu}R^2\left[1-\left(\frac{r}{R}\right)^2\right]$$

where $V_z$ is the velocity at radius r, L is the length of the pipe, $\Delta P$ is the pressure gradient (over length L), μ is the viscosity of the fluid, R is the radius of the pipe, and r ranges between 0 and R.

Figure 6C:
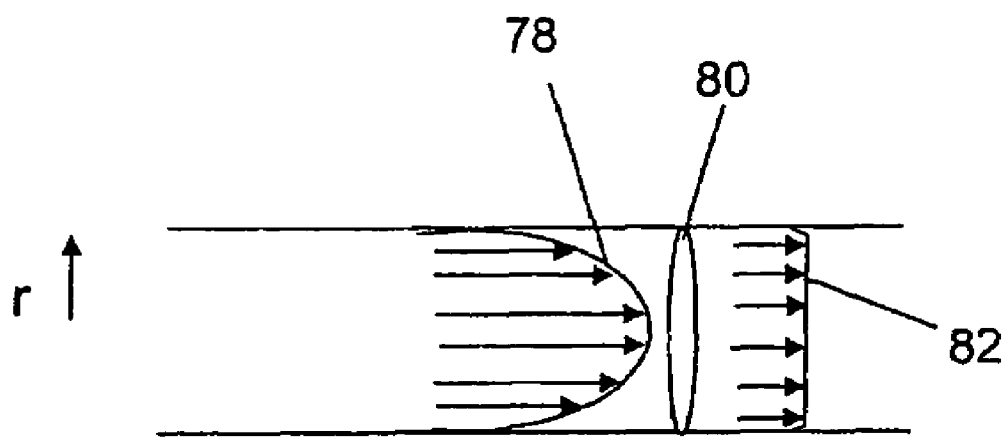

In order to avoid varying stresses upon the cell constructs at different distances from the longitudinal axis of the chamber (as a result of dissimilar velocities), a distributing fluid mesh (80) is situated at one longitudinal end of the chamber (26) in the inlet half (20') of the bioreactor (20) (FIG. 4). The mesh may be constructed from any material that is inert or biocompatible with the growth medium, and possesses the physical strength to withstand pressures of fluid flow. Preferred materials are Plexiglas™, polycarbonate or any solid transparent material. For reusable meshes, the material should resist sterilization by autoclaving. For disposable meshes (i.e. a single use) any inert material may be used. The pores of the mesh preferably have a diameter of up to 10 mm, and more preferably, a 2 mm diameter. The mesh (80) is utilized to equally distribute the velocity of the medium in the chamber (26) by interrupting the developed flow (78) before the medium reaches the cell constructs, thus providing an undeveloped laminar profile (82) and similar stresses on each cell construct (FIG. 6c).

The stress induced by the flowing medium upon the cell constructs in the bioreactor body, can be expressed by the following equation:

$\tau = F_D / S$

Where τ is the stress on each scaffold, $F_D$ is the drag force acting on the scaffold, and S is the surface area subjected to the stress.

$F_D$ is calculated as follows:

$F_D = 0.5\rho V^2 A C_D$

Where ρ is the fluid density, V is the fluid velocity, A is the cross section area of the scaffold, and $C_D$ is the drag coefficient, which, based on the relevant Reynolds number and the flow around a smooth cylinder, is 1.4 (see Potter M C and Wiggert D C, Mechanics of Fluids, Prentice Hall, Second Edition (1997) pp 341).
Thus:

$F_D = 1.24 * 10^{-5}$ kg*m/s$^2$

Since S is $\pi r^2 + h*2\pi r$ where h is the scaffold's height and r is its radius,
the stress acting on the scaffold is:

$\tau = 2.4$ dynes/cm$^2$

In the present system, a change in the flow rate (Q) will lead to different stresses in an exponential rate, on the cell constructs.

A mesh (80) may be placed in both the inlet (20') and outlet (20") halves of the chamber in order to be suitably configured for reversible operation, whereby the parameters in the computerized pump may be set to reverse the medium flow direction.

A computerized peristaltic pump (50), well known in the art and therefore, not shown in detail, provides mechanical stimulus to the cell constructs via pulsing the flow of the medium. During a typical operation, the peristaltic pump supplies between 0.5 and 5 ml of the culture medium at a rate of 150 ml/min. The interval between each pulse provided by the pump is 0.2 sec. Such operating parameters are selected to replicate the beating of a human heart.

Figure 7:
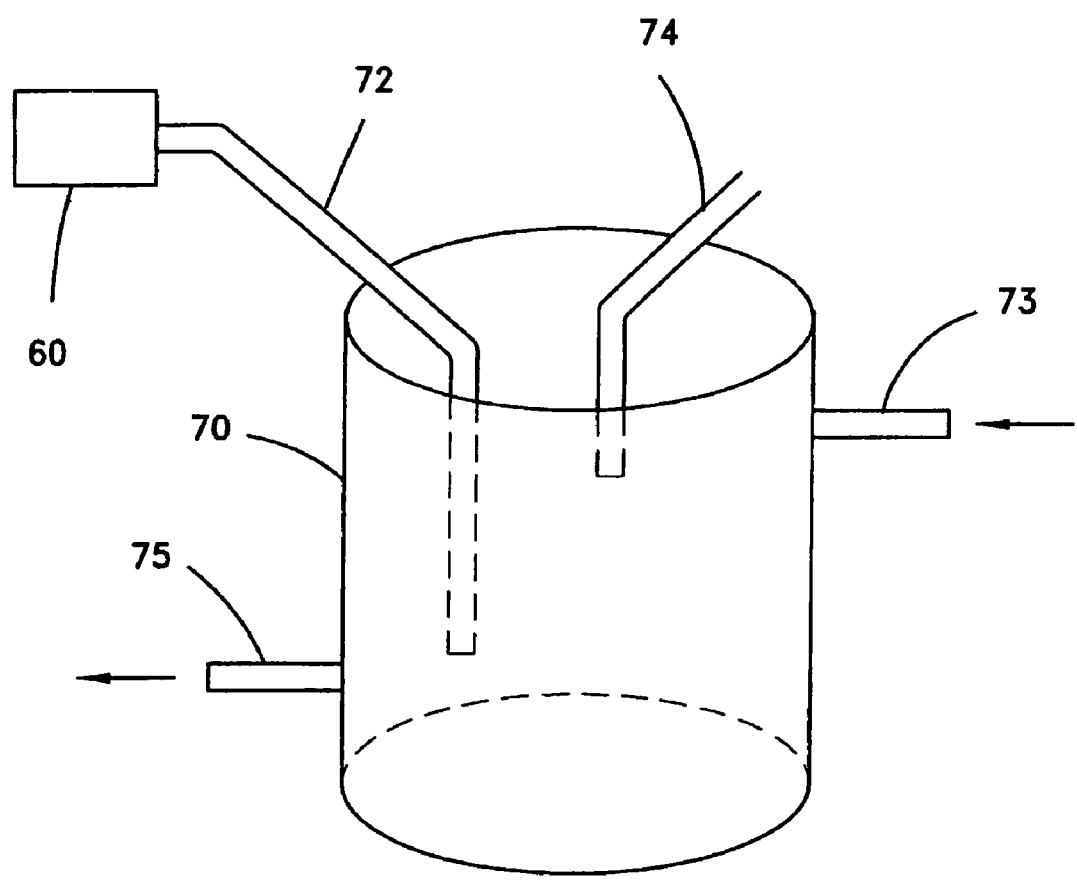
FIG. 7 illustrates a schematic representation of the preferred embodiment of the reservoir of the present invention.

A preferred embodiment of the reservoir (70) of the present invention is shown schematically in FIG. 7. The reservoir (70) wall is preferably made of Plexiglas™, but can alternatively be made of any suitable material such as glass or aluminum. The reservoir (70) is preferably 5 cm in diameter, but can range between 1 cm to 100 cm in diameter, and is preferably 20 cm high, but can range between 1 cm to 100 cm in height. A tube (72) for transferring gas through a filter (not shown) from a gas supply (60) to the reservoir (70) penetrates the top of the reservoir (70) to preferably between 60% to 80% of the reservoir's (20) depth, and more preferably to about 70% of the reservoir's (70) depth. Above the preferred range, the reservoir may not be homogenous, and deeper than the preferred range, the bubbles may interfere with the out-coming medium.

The tube (72) is also preferably made of Plexiglas™, but can alternatively be made of any suitable material such as glass or aluminum.

The gas supply (60) of a typical bioreactor system contains a composition of 21% $O_2$, 5% $CO_2$ and the remainder, N2, although different tissue growths may require different compositions. Constant pH, $PO_2$ and $PCO_2$ are preserved in the medium by regulating the flow of gas from the supply (60) to the reservoir (70), and are compatible with physiological levels. The reservoir (70) also comprises a gas outlet tube (74) for relieving the pressure that develops within the reservoir (70), and inlet (73) and outlet (75) tubes for transferring the medium to and from the bioreactor body (20). A medium sample collection outlet (not shown) is located on the inlet (73) and outlet (75) tubes for periodically removing small amounts of medium. The medium is tested to determine whether a significant amount of waste contained within it and/or nutrients have been depleted, and when necessary, the reservoir (70) is replaced with fresh medium. Transfer tubing (76) transfers medium from the reservoir (70) to the bioreactor (20), and back to the reservoir (70), as shown by the directional arrows.

A heat exchanger (40) (shown only in FIG. 1) is provided for maintaining constant temperature of the medium.

The oxygen mass transport rate from the incoming gas bubble to the medium in the reservoir is defined as:

$$OTR = \frac{dC_o}{dt} = k_L a(C_o^* - C_o)$$

where OTR is the oxygen transport rate, $C_o^*$ is the oxygen concentration at the bubble-medium interface, $C_o$ is oxygen concentration in the medium bulk, $k_L$ is the oxygen mass transport coefficient at the bubble-medium interface between the gas bubble and the medium and α is the surface area of the bubbles per medium volume. Since α is difficult to determine, the parameter $k_L\alpha$ is defined as the volumetric oxygen mass transport coefficient and may be determined by an oxygen electrode.

Control over the OTR can be achieved by a change in $C_o^*$ or $k_L\alpha$. Since $C_o^*$ is constant in the gas container, the variable parameter is $k_L\alpha$. In the present system $k_L\alpha$ may be changed by a change in the width of the gas inlet tube (72), since this changes the size of the bubble, and therefore induces a change in α.

Another factor effecting the oxygen concentration in the medium is the gas hold-up and the sustention time of the bubble in the system. Gas hold-up is defined as:

$$G_H = \frac{V_g}{V_g + V_l}$$

where $G_H$ is the gas hold-up, $V_g$ is the total volume of the bubbles within the reservoir and $V_l$ is the volume of the liquid in the system. High $G_H$ and sustention time (i.e. the period of time in which the bubble interacts with the liquid medium phase) can enhance oxygen mass transport to the medium on the one hand, but, on the other, hand may increase $CO_2$ concentration within the bubble, thus decreasing the oxygen mass transport. Optimization of these parameters leads to an efficient operation of the system.

Specific embodiments of the invention will be described by way of illustration in the following Examples. It will be understood that the invention can be carried out by persons skilled in the art with many modifications, variations and adaptations, without departing from its spirit or exceeding the scope of the claims.

Thus, for example, the following experiments were performed with cardiac cells, wherein the resulting tissue can be used as cardiac implant. Nonetheless, the bioreactor of the invention can be used for the preparation of different tissues structures. Tissue implants are widely used for the replacement of damaged or removed tissue and to facilitate the regeneration of tissue in defects caused by disease, trauma or reconstructive surgical procedures. Alginate scaffolds are generally used as implants, alone or seeded with cells for the purpose of cell and tissue transplantation. Furthermore, 3-D cell constructs may be used for the bioproduction of therapeutic proteins or for stem cell expansion.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Materials and Methods

Example 1

Proof of Medium Perfusion in the Bioreactor of the Present Invention

Figure 8:
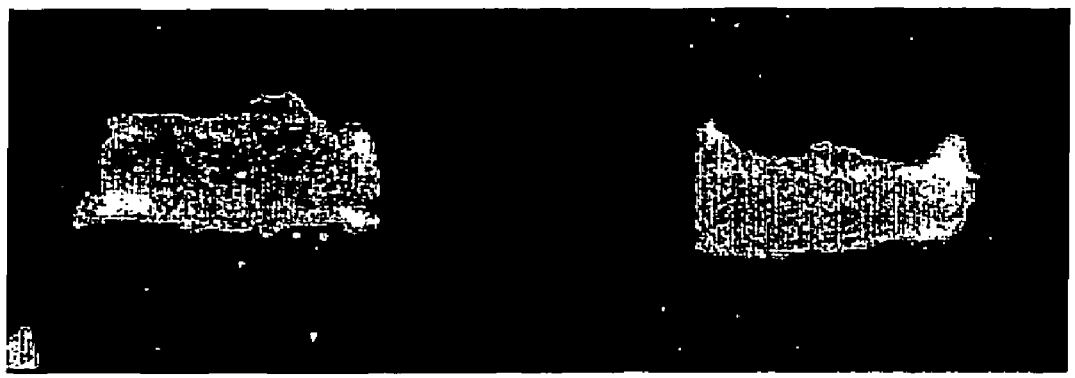
FIG. 8 illustrates slices of harvested and frozen cell constructs from Example 1.

The ability of the medium to perfuse into the cell constructs in the bioreactor of the present invention was investigated by following the distribution of 5-carboxyfluorescein (CF) (Sigma, Israel) in alginate cell constructs with the following dimensions, 5 mm×2 mm, d×h. Perfusion was achieved using a peristaltic pump, which pumped the medium at a rate of 150 ml/min. Cell constructs placed in a bioreactor under static conditions (i.e. with no medium flow) as well as in the bioreactor of the present invention were supplemented with a medium containing 0.5% (w/v) CF. After 1 minute, the cell constructs were harvested, frozen and longitudinally sliced to 0.5 mm thick slices. The slices were viewed under a fluorescent microscope and photographed (FIG. 8). There is clear evidence that mass transport in cell constructs subjected to a perfused medium is higher than in cell constructs cultivated in static medium.

Example 2

Figure 9:
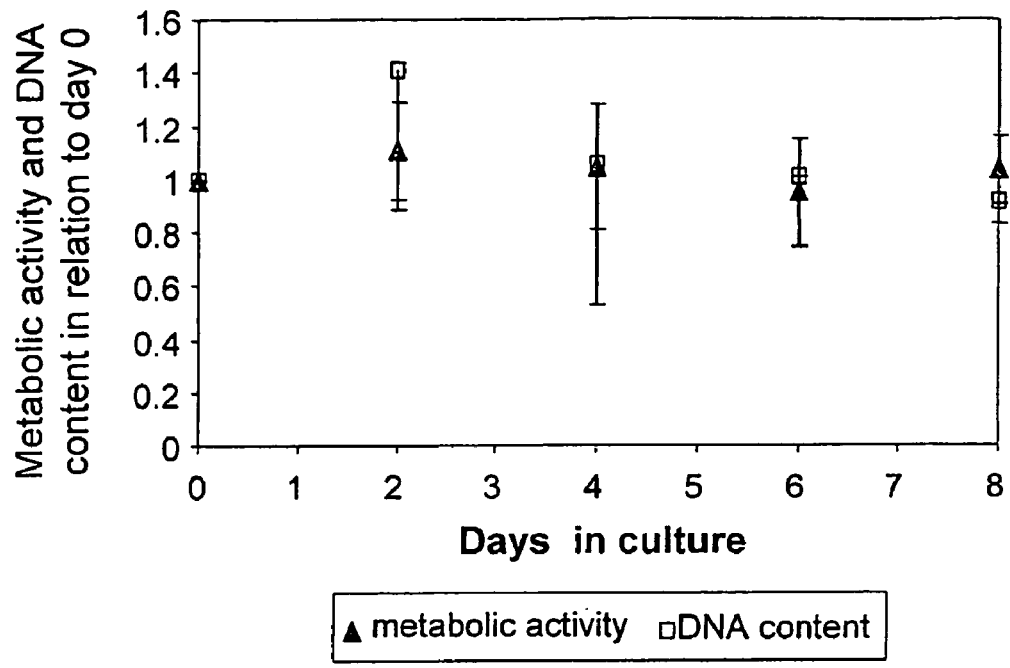
FIG. 9 graphically illustrates the results of Example 2, utilizing a bioreactor of the present invention.

Effect of the Bioreactor System of the Present Invention on Cardiac Cell Viability Alginate cell constructs (5 mm×2 mm, dia.×thickness) seeded with cardiac cells ($7\times10^5$ cells/construct) were cultivated within the bioreactor of the present invention for 8 days. The alginate scaffold of the alginate cell construct was prepared as described in WO97/44070 [see also Zmora, S. et al., Tailoring the pore architecture in 3-D alginate scaffolds by controlling the freezing regime during fabrication. Biomaterials (2002), 23(20), 4087-4094]. Samples (n=2-3 per data point) were taken every 2 days and MTT (Biological Industries, Israel) and Hoechst 33258 (Sigma, Israel) assays were performed to determine metabolic activity and DNA content. The results shown in the graph of FIG. 9, wherein the x-axis shows time in units of days in the culture, and the y-axis shows the metabolic activity and DNA content in relation to day-0, show high maintenance of over 90% of the initial cell number. Triangular points represent metabolic activity, and square points represent DNA content.

The alginate cell constructs may also be seeded with different cell types such as stem cells (embryonic and adult, from different sources), hepatocytes, chondrocytes, skin, muscle, endothelial cells, cardiac cells, cell lines used for protein bioproduction, hybridoma cells, etc.

Figure 10:
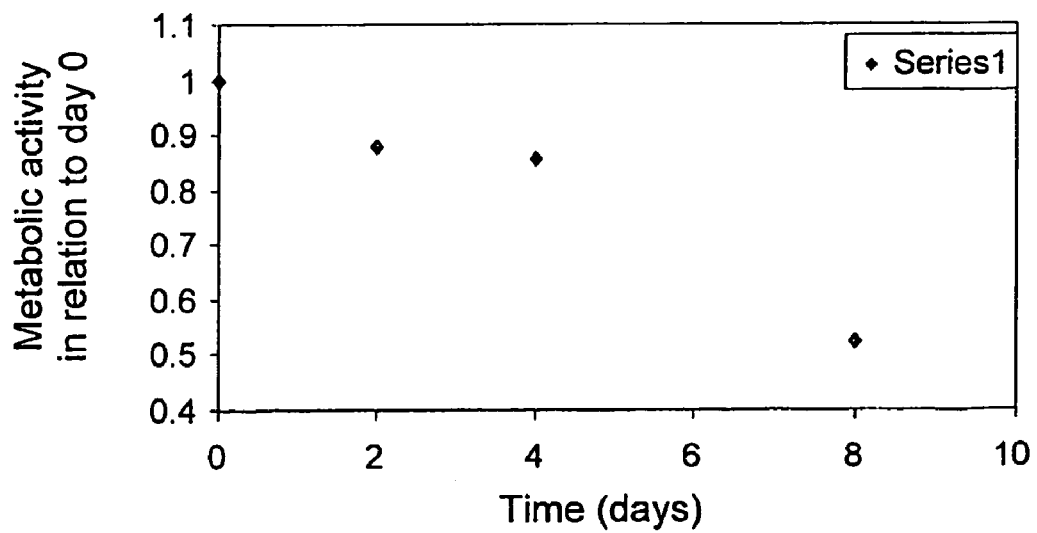
FIG. 10 graphically illustrates the results of Example 2, utilizing a static cell cultivation vessel.

In the static cultivation (results shown in FIG. 10), wherein one seeded scaffold was placed in a 1 ml CM+ medium (M199 medium) (Biological Industries, Israel) with 5% (v/v) fetal calf serum (Biological Industries, Israel), supplemented with 0.6 mM $CuSO_4.5H_2O$, 0.5 mM $ZnSO_4.7H_2O$, 500 U/mL Penicillin and 100 µg/mL streptomycin (all Biological Industries, Israel) the decline in cell number over time was pronounced, especially between days 4 and 8. The x-axis of the graph in FIG. 10 shows the time in units of days, and the y-axis shows the metabolic activity in relation to day-0.

Example 3

Figure 11:
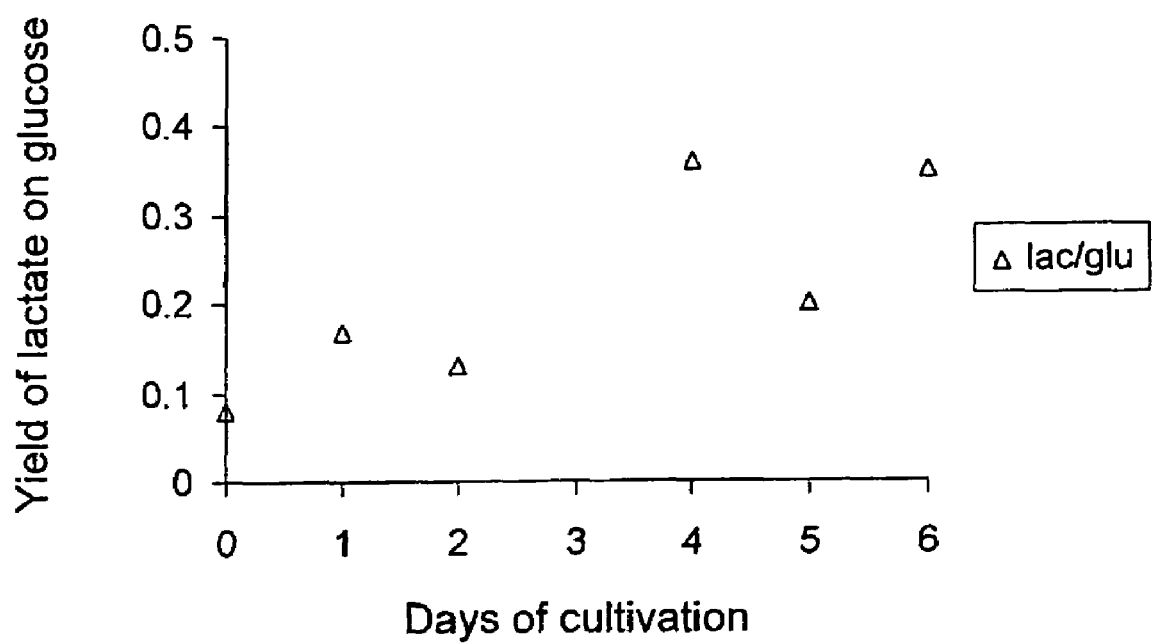
FIG. 11 graphically illustrates the results of Example 3, showing aerobic cell metabolism (yield of lactate on glucose).

Metabolic Indices of Medium in the Bioreactor System of the Present Invention A 0.5 ml CM+ medium from the bioreactor system of the present invention was sampled each day and analyzed for glucose and lactate using a gas blood analyzer. The graph in FIG. 11 shows the yield of lactate on glucose ($Y_{L/G}$) (y-axis), calculated as a molar ratio of the produced lactate and utilized glucose over time (x-axis) in terms of days. The ratio reveals aerobic cell metabolism. The values were calculated as molar ratios of produced lactate and utilized glucose.

Example 4

Figure 12:
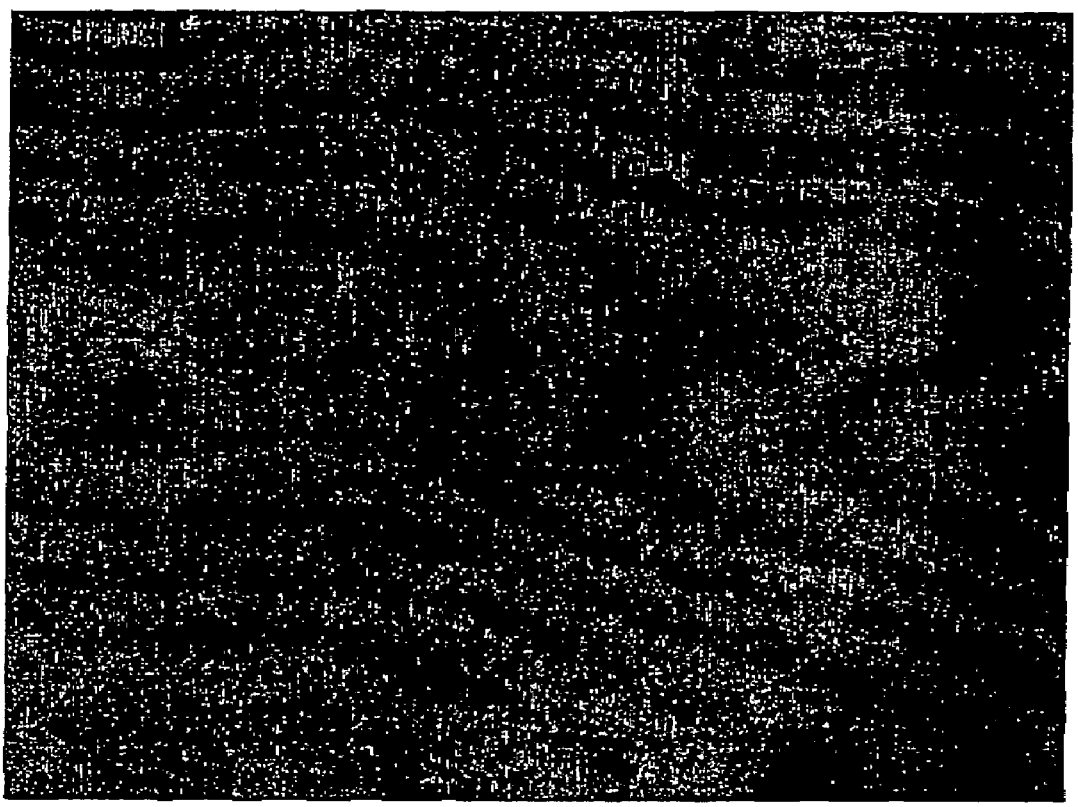
FIG. 12 illustrates viable cell clusters in cell constructs cultivated by the bioreactor of the present invention (Example 4).

Effect of the Bioreactor System of the Present Invention on Cardiac Cell Distribution in Alginate Cell Constructs Staining 7-day cardiac constructs cultivated in the bioreactor system of the present invention with both FDA (Sigma Israel) (fluorescein diacetate) and PI (Sigma Israel) (propidium iodide) revealed viable cell clusters formed at the center of the cardiac construct (FIG. 12).

Figure 13:
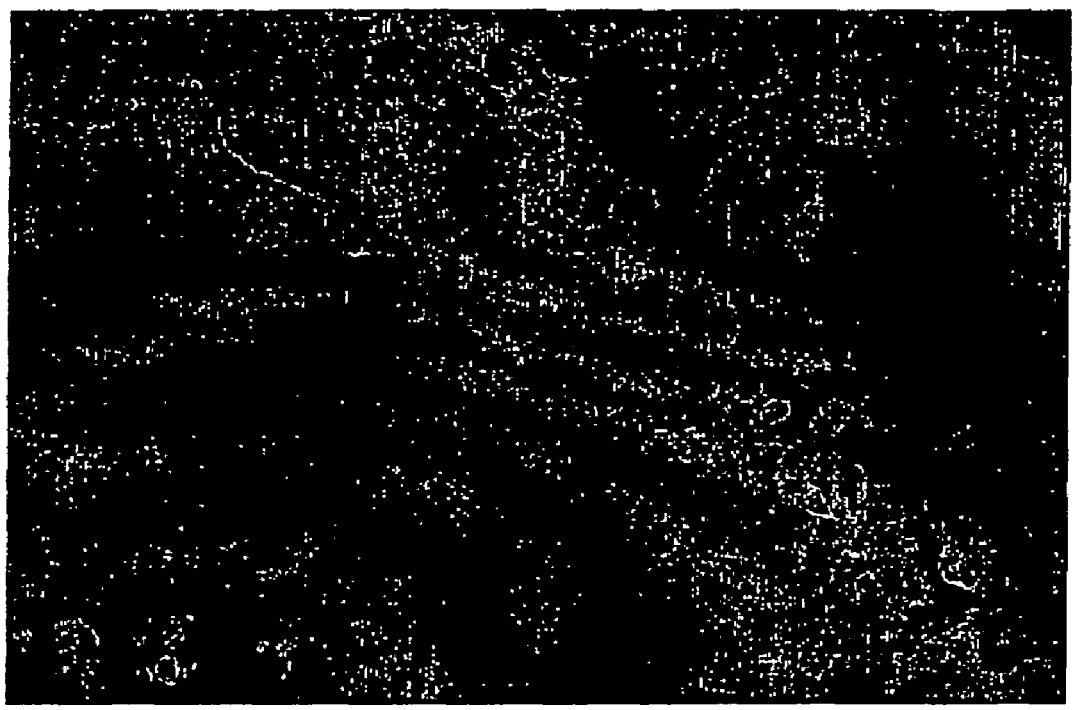
FIG. 13 illustrates a large viable cardiac tissue in a construct cultivated in accordance with the present invention (Example 4).

At day 14, the clusters appear to develop into a viable cardiac tissue with a thickness of larger than 100 μm (i.e. the limiting distance of oxygen diffusion under atmospheric pressure) (FIG. 13).

Figure 14:
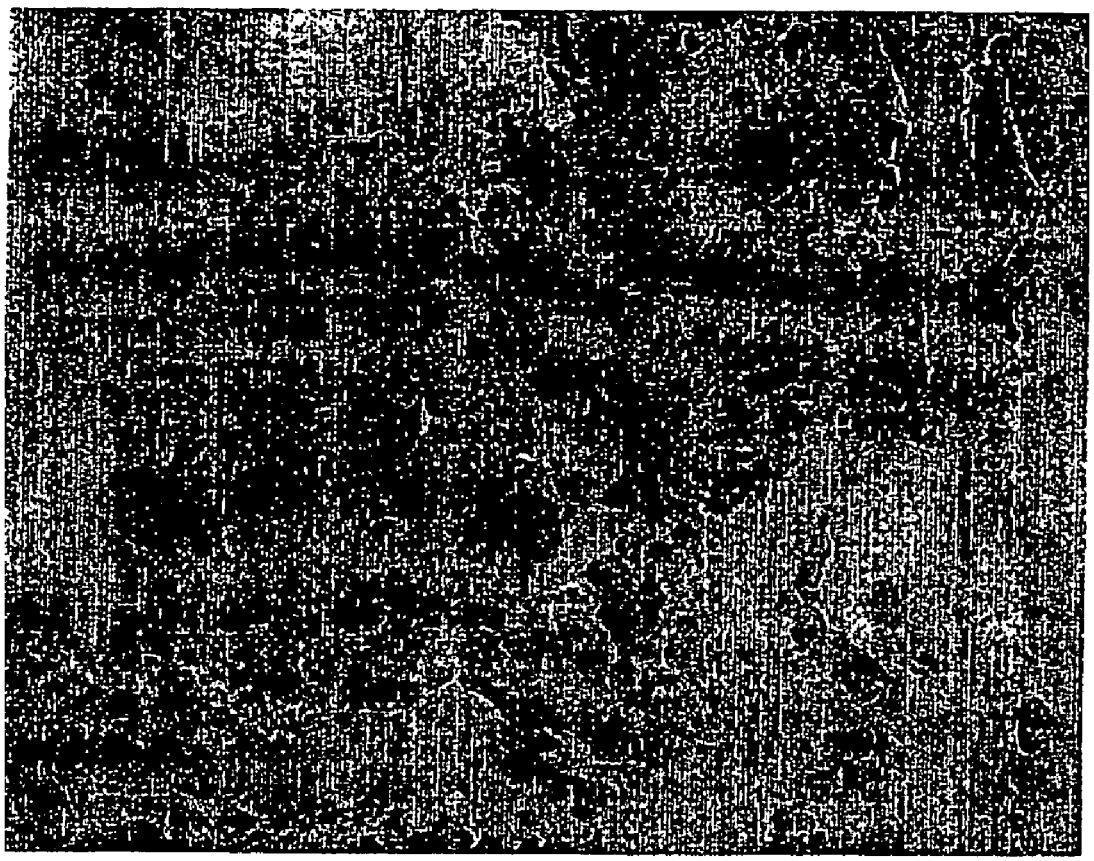
FIG. 14 illustrates H&E (hematoxylin-eosin) stained thin cross-sections of cultivated cardiac cell constructs from Example 4.

Hematoxylin-Eosin (H&E) staining of thin sections (5 μm thickness) from the cardiac constructs cultivated in the bioreactor system of the present invention for 14 days revealed the formation of large cardiac tissue (FIG. 14).

The invention claimed is:

1. A net for supporting one or more cell constructs in the culture chamber of a bioreactor, comprising an array of impermeable pyramidal elements protruding from the face of said net, wherein each of the corners of the base of each of said impermeable pyramidal elements comprises a circular opening.

2. The net according to claim 1, wherein the diameter of said circular opening is between 0.1 mm to 3 mm.

3. The net according to claim 1, wherein the distance between any two adjacent circular openings situated orthogonally to one another along the x- or y-axis is between 1 mm to 10 mm.

4. The net according to claim 1, wherein the angle of the outer edges of the pyramidal elements is between 1° to 179°.

5. The net according to claim 1, wherein said net is constructed from a material selected from the group consisting of poly(methyl methacrylate), polycarbonate or any solid transparent material.

6. A bioreactor comprising an inlet half having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and further comprising at least one net for supporting one or more cell constructs in the culture chamber of a bioreactor, comprising an array of impermeable pyramidal elements protruding from the face of said net, wherein each of the corners of the base of each of said impermeable pyramidal elements comprises a circular opening, wherein said net is positioned transversely within said culture chamber.

7. The bioreactor according to claim 6, wherein said culture chamber is cylindrical in shape.

8. The bioreactor according to claim 7, wherein said net is circular.

9. The bioreactor according to claim 7, wherein the diameter of said net is equal to the diameter of said culture chamber.

10. The bioreactor according to claim 6, wherein two identical said nets are positioned transversely within said culture chamber.

11. The bioreactor according to claim 10, wherein at least one of said nets is permanently affixed to the circumference of said culture chamber.

12. The bioreactor according to claim 10, comprising means for removably affixing at least one of said nets within said culture chamber.

13. The bioreactor according to claim 12, wherein said means comprises a projection which protrudes inward from the circumference of said culture chamber wall.

14. The bioreactor according to claim 6, wherein said inlet aperture is threaded for suitably attaching means for transferring a fluid medium to said culture chamber.

15. The bioreactor according to claim 6, wherein said outlet aperture is suitably threaded for attaching means for transferring fluid medium from said culture chamber.

16. The bioreactor according to claim 14, wherein said means comprise transfer tubing.

17. The bioreactor according to claim 6, wherein said inlet half and said outlet half are joined to each other via screws or bolts.

18. The bioreactor according to claim 6, wherein the means for sealing said inlet half with said outlet half comprises an O-ring.

19. The bioreactor according to claim 6, wherein a fluid distributor mesh is positioned in said inlet half between said inlet aperture and said net.

20. The bioreactor according to claim 19, wherein a fluid distributor mesh is positioned in said outlet half between said outlet aperture and said net.

21. The bioreactor according to claim 20, wherein any of said fluid distributor meshes comprise pores whose diameter is up to 10 mm.

22. The bioreactor according to claim 6, wherein said bioreactor may be used for bioproduction of therapeutic protein.

23. The bioreactor according to claim 6, wherein said bioreactor may be used for stem cell expansion.

24. A bioreactor system comprising:
   a. a bioreactor comprising an inlet halt having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and comprising two identical nets for supporting at least one cell construct in said chamber, wherein the distance between said nets is equal to the thickness of said at least one cell construct, wherein each of said nets comprises an array of pyramidal elements protruding from the face of said net, wherein the vertex of each of said pyramidal elements comprises a circular opening
   b. a culture medium reservoir for storing a supply of a fluid culture medium, comprising a medium inlet and outlet, and further comprising a gas inlet and outlet;
   c. a gas supply for supplying gas to said medium contained in said reservoir,
   d. a heat exchanger for maintaining the temperature of said medium at a constant value, and e. a pump for pumping said medium from said reservoir into said bioreactor and back to said reservoir.

25. The bioreactor system according to claim 24, wherein said reservoir comprises a medium sample collection outlet.

26. The bioreactor system according to claim 24, wherein said pump is a peristaltic pump.

27. A method for the cultivation of 3-D cell constructs, comprising the following steps:
   a. providing a bioreactor system comprising
      i. a bioreactor, said bioreactor comprising an inlet half having an opening at one end and an inlet aperture at its opposite end, and an outlet half having an opening at one end and an outlet aperture at its opposite end, wherein said halves are joined at their opening ends such that the hollow interior of said bioreactor forms a culture chamber, and comprising two identical nets for supporting at least one cell construct in said chamber, wherein the distance between said nets is equal to the thickness of said at least one cell construct, wherein each of said nets comprises an array of pyramidal elements protruding from the face of said net, wherein the vertex of each of said pyramidal elements comprises a circular opening;
      ii. a culture medium reservoir for storing a supply of a fluid culture medium, comprising a medium inlet and outlet;
      iii. a gas supply for supplying gas to said medium contained in said reservoir;
      iv. a heat exchanger for maintaining the temperature of said medium at a constant value; and
      v. a pump for pumping said medium from said reservoir into said bioreactor and back to said reservoir;
   b. placing at least one cell construct within said culture chamber, between said nets;
   c. pumping said medium from said reservoir into said culture chamber, thereby causing medium perfusion into said cell construct for a suitable period of time; and
   d. harvesting the resulting construct.

28. The method according to claim 27, further comprising:
   e. removing a sample of said medium from said reservoir after step c and before step d, in order to determine whether said medium should be replaced with new medium;
   f. adding fresh medium to said reservoir when necessary, after step e and before step d.

29. The method according to claim 27, wherein said cell construct consists of a polymeric scaffold seeded with cells.

30. The method according to claim 29 wherein said polymer is a polysaccharide.

31. The method according to claim 29, wherein said cells are human cells.

32. The method according to claim 27, wherein said 3-D cell constructs are for the bioproduction of therapeutic proteins.

33. The method according to claim 27, wherein said 3-D cell constructs are for stem cell expansion.

34. The net according to claim 2 wherein the diameter of said circular opening is 1.25 mm.

35. The net according to claim 3, wherein the distance between any two adjacent circular openings situated orthogonally to one another along the x- or y-axis is 3 mm.

36. The net according to claim 4, wherein the angle of the outer edges of the pyramidal elements is 60°.

37. The bioreactor according to claim 21, wherein any of said fluid distributor meshes comprise pores whose diameter is 2 mm.

38. The method according to claim 30 wherein the polysaccharide is alginate.

39. The method according to claim 31 wherein the human cells are cardiomyocytes.

* * * * *